United States Patent [19]

Sayce et al.

[11] 3,969,280

[45] July 13, 1976

[54] SOLID AIR FRESHENER GELS

[75] Inventors: John G. Sayce, Headly; David J. Brown, Sandhurst, Camberley, both of England

[73] Assignee: S. C. Johnson & Son, Inc., Racine, Wis.

[22] Filed: Apr. 3, 1975

[21] Appl. No.: 564,970

[30] Foreign Application Priority Data

Mar. 7, 1975  United Kingdom................ 9616/75

[52] U.S. Cl.................................. 252/522; 424/76
[51] Int. Cl.$^2$........................................... A61L 9/00
[58] Field of Search .............. 252/522; 424/76, 333; 260/25 R

[56] References Cited
UNITED STATES PATENTS

| | | | |
|---|---|---|---|
| 2,169,055 | 8/1939 | Overshiner.......................... | 252/522 |
| 2,691,615 | 10/1954 | Turner et al........................ | 424/76 |
| 2,927,055 | 3/1960 | Lanzet................................ | 424/76 |
| 3,220,960 | 11/1965 | Wichterle.......................... | 260/2.5 R |
| 3,400,890 | 9/1968 | Gould................................ | 252/522 |
| 3,567,119 | 3/1971 | Wilbert.............................. | 252/522 |
| 3,596,833 | 8/1971 | Gould................................ | 252/522 |
| 3,688,985 | 9/1972 | Engel................................. | 252/522 |
| 3,886,125 | 5/1975 | Chromecek........................ | 424/76 |

Primary Examiner—Veronica O'Keefe

[57] ABSTRACT

An improved air freshener gel which is substantially syneresis-free comprising in an aqueous system from 0.5–10% by weight of CMC, 0.01–10% by weight perfume, a source of trivalent cations selected from chromic ion, aluminum ion or mixtures sufficient to produce a weight ratio of CMC to effective weight of trivalent cation of 1:0.01 to 1:0.1 and water.

10 Claims, No Drawings

SOLID AIR FRESHENER GELS

BACKGROUND OF THE INVENTION

This invention relates to solid air freshener compositions. More particularly, this invention relates to a solid air freshener gel composition utilizing a cross-linked carboxymethyl cellulose as the primary gelling agent.

During recent years, a number of solid air freshener compositions have been marketed with a reasonable degree of success. These compositions, which are primarily based on carrageenan, release perfume or freshening agent continuously over a period of time. Although carrageenan adequately forms gels and is capable of entrapping perfumes for slow release, the physical properties of the carregeenan gel create a number of problems which must be closely watched during production and formulation. One of the most important problems regarding carregeenan is a problem known as syneresis, i.e., the loss of moisture from the gel to the surface which gives the gel a wet appearance and can create difficulties. The syneresis problem can be alleviated in carrageenan gels by using sufficiently high percentages of the carregeenan gelling agent. However, carregeenan is an expensive material and it is very difficult to produce an economic solid air freshener gel without having significant amounts of syneresis.

Attempts have been made to alleviate this syneresis problem by incorporating various additional metal ions, such as potassium ions, into the composition. Also, attempts have been made to increase the stability of these materials and decrease syneresis by adding other thickeners, such a guar gum and gelatin, to the system. An example of compositions of the above type are U.S. Pat. 2,927,055 and British Patent 1,241,914. However, compositions within the scope of the above patents tend to produce some degree of syneresis depending upon the amount of carrageenan utilized and, accordingly, a satisfactory gel is difficult and expensive to produce.

In addition to the syneresis problem, the prior art carrageenan systems are difficult to produce in large volumes. These systems are heat sensitive gels and, accordingly, production requires both heating and cooling means for proper mixing and processing. These heating and cooling means add significantly to the costs of these prior art systems and further require careful monitoring of the process.

It has been discovered that a known characteristic of carboxymethyl cellulose, i.e., when certain trivalent metal cations are added to CMC they will cross-link the carboxymethyl cellulose to form a gel, can be used to form an effective, inexpensive air freshener gel. Examples of disclosures relating to CMC gels are U.S. Pat. 3,749,174, which discloses the utilization of sodium carboxymethyl cellulose and chrome potassium sulfate gels in drilling muds, British Patent 1,163,518, which discloses a method of laying pipe which includes filling the trench with an aqueous carboxymethyl cellulose solution loaded with sand and including aluminum sulfate, "Industries Gums" by J. W. BeMiller, Academic Press, New York, 1973, pp. 716–7, and a publication of Hercules Chemical entitled "Cellulose Gum-Sodium Carboxymethyl cellulose" copyrighted 1971.

BRIEF DESCRIPTION OF THE INVENTION

It has been discovered that a stable air freshener gel having a low degree of syneresis and an effective perfume generation profile can be produced utilizing a composition from 0.5–10% by weight sodium or potassium carboxymethyl cellulose, from 0.01–10% by weight perfume, from 0.05–10% by weight of a surfactant material selected from nonionic surfactants and gum surfactants, a source of a trivalent metal cation sufficient to produce a weight ratio of carboxymethyl cellulose to effective weight of trivalent cation of from 1:0.01 to 1:0.1 and water.

It is, therefore, the primary object of the present invention to provide a low-cost air freshener gel having a limited degree of syneresis.

It is a further object of the present invention to provide an air freshener gel utilizing as the primary gelling agent carboxymethyl cellulose cross-linked with a trivalent metal cation.

It is a still further object of the present invention to provide an inexpensive and effective solid air freshening gel composition capable of supporting its own weight.

It is a still further object of the present invention to provide an air freshener gel which is simple and economical to produce.

Still further objects and advantages of the composition and method of the present invention will become more apparent from the following, more detailed description thereof.

DETAILED DESCRIPTION OF THE INVENTION

The air freshener gels of the present invention comprise from 0.5–10% of sodium or potassium carboxymethyl cellulose, from 0.05–10% of a surfactant, from 0.01–10% of a perfume, a source of trivalent metal cation selected from aluminum ions and chromic ions sufficient to give a ratio of CMC to effective weight of trivalent cation of 1:0.01 to 1:0.1 with the balance being water.

The method of the present invention comprises exposing a gel having a composition comprising 0.5–10% sodium or potassium carboxymethyl cellulose, perfume, a surfactant, a source of trivalent metal ion, and water to the atmosphere and allowing the gel to evaporate over a period of time releasing the perfume.

Carboxymethyl cellulose is generally sold as the sodium or potassium salts and is produced by reacting alkali cellulose with sodium or potassium monochloroacetate under rigidly controlled conditions. Cellulose has a polymer structure with anhydroglucose units linked to each other through ether bonds. Carboxymethyl cellulose, or CMC as it will be referred to herein, is cellulose wherein carboxymethyl groups have been attached to some of the hydroxy groups by an ether linkage. CMC can be prepared in a variety of weight average molecular weights from about 20,000 to about 1 million. There are three hydroxy groups on each anhydrogluclose unit which can have the hydroxy hydrogen replaced by a sodium carboxymethyl groups. The degree of substitution is the average number of hydroxy groups replaced over the length of the chain with carboxymethyl groups. The solubility of the polymer in water is in part a function of the degree of substitution, i.e., the more highly substituted the polymer, the more water-soluble it becomes. In addition, it has been found that more flexible gels can be prepared using CMC with higher degrees of substitution. Also, commercially available carboxymethyl cellulose polymers are provided with different degress of purity. Some grades of CMC contain only 65% carboxymethyl cellulose, while others contain about 95–99% pure material. Although it is not critical for proper performance of the air freshener gels of the invention, it is preferred to utilize purer materials since extraneous salts and other materials which may be present in the less pure grades of carboxymethyl cellulose can interfere to some degree with the desirable characteristics of the gels.

The viscosity of the carboxymethyl cellulose is primarily dependent on the molecular weight of the polymer and is also affected to some small degree by the degree of substitution. The viscosity of the CMC as such is not critical to the performance of the air freshener gels of the present invention. The primary effect of the viscosity on the gel compositions of the present invention is that a higher molecular weight and more viscous CMC tends to form gels at a lower concentration of CMC than CMC polymers having a lower molecular weight and, accordingly, lower viscosity.

Although the viscosity of the CMC can be varied to meet the parameters of various processing techniques, occasionally it may be desirable to use a larger amount of a less viscous gel to form the air freshener gels of the present invention. However, the choice of the particular viscosity for the processing conditions to be utilized is something within the skill of those familiar with the physical properties of carboxymethyl cellulose.

As has been stated previously, it is known that when a source of various trivalent metal cations is added to carboxymethyl cellulose a gel-like structure is formed. However, it has been found that out of the number of trivalent cations possible only chromic ions, aluminum ions and mixtures of chromic and aluminum ions are suitable for forming air freshener gels. The other trivalent cations form gels which set up or gel instantaneously and/or are too brittle for use as an air freshener gel. Chromic cations and mixtures of chromic and aluminum ions are preferred since aluminum alone tends to form gels too rapidly and also forms gels having a higher degree of brittleness than chromic ion gels. It is most preferred to utilize a source of chromic ions as the sole cross-linking agent for the CMC since the gel formation is easily controlled and a firm, yet flexible, gel is formed.

In order to form acceptable gels which will function as air fresheners, it is necessary to utilize a sufficient source of a trivalent chromic and/or aluminum cation to produce a ratio of CMC to effective weight of trivalent cation of from 1:0.02 to 1:0.1, and preferably from 1:0.03 to 1:0.06.

The term "effective weight of trivalent cation" as used in this specification and in the attached claims means the grams of trivalent cation available from a particular source of trivalent cation as defined by the formula $$\frac{M}{M_2O_3} \cdot Y = \frac{\text{effective weight}}{\text{gm of source of ion}}$$

wherein M is the molecular weight of the trivalent cation, $M_2O_3$ is the molecular weight of the oxide of the cation and Y is the percent oxide by analysis in the source material. For example, one gram of basic chrome sulfate having a $Cr_2O_3$ content of 33% contains about 0.226 gm of $Cr^{+3}$.

Suitable sources of the chromic ion include basic chrome sulfate and chromium acetate, while suitable sources of the aluminum cation include aluminum citrate, basic aluminum sulfate and aluminum acetate. Other sources of trivalent chromium and aluminum also can be used to manufacture the compositions of the present invention. The particular anions which are present do not appear to appreciably interfere with gel formation. Some anions are particularly useful since they limit the release of the cations for gel formation.

It is not completely appropriate to specify a particular amount of these cation donating materials since various grades and types of these materials vary widely in cation content per gram. For example, some types of commercially available basic chrome sulfate contain 15% $Cr_2O_3$ while others have up to 30 or 35% $Cr_2O_3$. For this reason, the ratio of CMC to effective weight of trivalent cation is given since this is the critical parameter and can be readily determined for any material by analysis. For commercial meterials, generally from 0.1–1.5% by weight of the total composition will be the source of cations.

The composition of the present invention also includes a perfume. Perfumes generally are available from a series of perfume houses and are proprietary substances of a complex nature containing a series of various aromatic oils. Generally, these materials are alcohol- or oil-soluble, although water-soluble perfumes also are acceptable in the composition of the present invention. The level of perfume in the composition is not particularly critical so long as the level is high enough to emit effective levels over the useful gel life. Generally from 0.01–10% is effective.

In order to enable the perfume to adequately be dispersed in the CMC gel of the present invention, a small amount, i.e., from 0.05–10%, of a surfactant material should be utilized. Preferred surfactant materials are of the nonionic type; however, it is possible to utilize some cationic surfactants. Anionic surfactants generally are not suitable since this type usually interferes with the formation of the gel structure. Examples of suitable nonionic and cationic surfactants can be found in McCutcheon's *Detergents and Emulsifiers, North American Edition* 1974 and *International Edition* 1974, published by Allured Publishing Corp., Ridgewood, N.J., USA, the disclosures of which are herein incorporated by reference. The particular surfactant used is not critical and will vary depending on the particular perfumes used. It is important to utilize some surfactant material in the present compositions to evenly disperse the perfumes throughout the gel.

Also suitable as surfactants and as total or partial replacements for the nonionic surfactants are various surfactant gum-like materials, such as nonionic hydrocolloids including hydroxylated guar gum and other similar gums or thickeners such as hydroxy cellulose. These meterials, although generally thought of as thickening agents, also have a sufficient degree of surfactant properties to evenly disperse the perfume throughout the air freshener gel composition of the present invention. Also, these materials can function as secondary thickeners.

The gels of the present invention are aqueous gels and water comprises from 75–99% and preferably from 80–90% of the total composition. It is suitable to use ordinary tap water since the small percentage of ions normally present do not adversely effect the gels of the present invention. Of course, deionized or distilled water could be used if desired.

Occasionally, it is necessary also to incorporate a small amount of a sequestering agent which slows the rate at which the trivalent metal cations react with the carboxymethyl cellulose to cross-link the same, especially when aluminum cations are used. Care should be exercised, however, in incorporating large amounts of sequestering agents since large amounts will prevent the formation of a suitable gel. Generally from 0–0.5% is suitable.

The air freshener gel may contain small amounts, generally less than 15% total, of various other optional ingredients such as various solvent, such as ethyl alcohol and methyl alcohol, low-boiling hydrocarbon fractions, second thickeners such as bentonite, locust bean gum, gum tragacanth, cellulose derivatives, preservatives, dyes or colorings so as to enable the product to have an overall aesthetic appeal. Care should be exercised since large amounts of some materials can adversely effect gel performance. It is preferable, but not necessary, for more even and fuller perfume release to utilize from 1–7% of a lower, i.e., $C_1$ to $C_4$, monohydric alcohol in the composition.

The compositions of the present invention are sufficiently rigid so as to be generally free-standing yet are sufficiently flexible to resist crumbling or breaking. These materials do not require a central core of other material to support the same, but can be poured directly into a container which can be maintained in an upright condition. The gels generally have sufficient strength so that they will not sag but will be maintained in the container so that air can easily and freely contact the surface of the same to transfer the perfume to the surrounding room. If it is desirable, however, to form the air freshener gel in a tub or other container without regard to the rigidity, the amounts of material can be reduced significantly to form a gel which will be sufficiently rigid so as not to flow out of the container if tilted, yet cannot be said to be sufficiently self-supporting to enable the same to be packed in a relatively cylindrical or upright container having openings near the bottom.

In order to prepare the air freshener gels of the present invention, it is a relatively simple matter of incorporating the various preservatives, dyes, perfumes and other components into an aqueous dispersion of the carboxymethyl cellulose and adding to this solution an aqueous solution containing the trivalent metal cation. Unlike the carrageenan gels of the prior art which required high temperatures followed by quick cooling to form the gel, the gels of the present invention are quickly formed by the reaction of the trivalent cation with the carboxymethyl cellulose; and, accordingly, no expensive heating or cooling equipment is necessary, the only equipment necessary being a sufficiently large container equipped with an agitator to insure complete mixing of the ingredients during reaction. The mixed materials are then poured into individual containers while they are still fluid and allowed to react in place to form a non-sagging solid gel.

While temperature is not critical to the formation of the gels of the present invention, as with prior art carrageenan gels, very high or very low temperatures should be avoided since the reaction to form the gel could be adversely effected. Also, extremes of pH should be avoided. The present gels are slightly acid, having a pH in the range of 5.0 to 6.9.

The composition and method of freshening the air of the present invention will not be described in more full detail by the following examples which are for the purposes of illustration only and are in no way to be considered as limiting.

EXAMPLE 1

A solid air freshener gel was prepared from the following formulation:

| Intermediate A | |
|---|---|
| Water | 72.65 |
| Preservative | 0.05 |
| Sodium CMC (ICI Cellofos B50) | 3.00 |
| Intermediate B | |
| Water | 19.86 |
| Dye | 0.10 |
| Nonionic surfactant (Triton X100) | 2.00 |
| Perfume | 2.00 |
| Basic chrome sulfate (33% $Cr_2O_3$) | 0.30 |
| Sodium hexametaphosphate | 0.04 |
| | 100.00 |

The formulation is prepared by first preparing Intermediates A and B as indicated above. Intermediate A is prepared by adding the preservative to water while being agitated and stirred vigorously, followed by gradually adding the carboxymethyl cellulose to the water preservative mix with stirring to form a thick, clear liquid. Intermediate B was prepared by first dissolving the dye in water to make a dye-water solution and also dissolving the sodium hexametaphosphate in water to make a solution of this material. These solutions are added together, followed by the addition of the nonionic surfactant, perfume and the basic chrome sulfate, all with good agitation. Intermediate B is then added to Intermediate A with good mixing and this combined formula is poured into containers. The formulation forms a firm yet flexible gel in approximately 30 minutes. Upon standing, this gel formed substantially no syneresis within 72 hours and released perfume at an adequate level over an extended period of time.

EXAMPLE 2

Example 1 was repeated with the exception that the sodium hexametaphosphate is eliminated from the composition with a proportionate increase in the water content. This formulation performed as in Example 1 with the exception that the setting or gelling time was reduced to approximately 15 minutes.

EXAMPLE 3

Example 1 was repeated with the exception that the chrome content was increased to 0.9% and the water level was decreased an appropriate amount. When this sample was prepared in accordance with the procedure of Example 1 and poured into air freshener containers, the same formed an acceptable gel with a low degree of syneresis. The ratio of CMC to trivalent cations utilized in this example is 1:0.06.

EXAMPLE 4

The procedure of Example 1 was followed with the exception that the 33% basic chrome sulfate was replaced with 0.3 g. 15% basic chrome sulfate to give a CMC to trivalent cation oxide ratio of 1:0.0103. The resulting gel set within 30 minutes and formed gel which sagged. However, no syneresis was produced. Although this gel would not be satisfactory for use in a self-standing, upright container, it would be satisfactory if the gel was completely supported by the container.

EXAMPLE 5

A blend of carboxymethyl cellulose, chrome and water was prepared to show that high levels of trivalent cation produce syneresis. The following composition was prepared:

| | |
|---|---|
| 1.5% | Sodium CMC |
| 0.5% | Basic Chrome sulfate (33%) |
| 98.0% | Water |

The ratio of CMC to trivalent cation is 0.075; and, although this produced a strong rigid gel, there was evidence of syneresis evident after only 24 hours. Therefore, although this could be used for some systems, the level of syneresis is not completely desirable.

EXAMPLE 6

A composition having the following formulation was prepared:

Intermediate A
| | | |
|---|---|---|
| 3.0 | parts by wt. | Sodium carboxymethyl cellulose |
| 0.3 | part by wt. | Hydroxylated guar gum |
| 0.2% | | Preservative |
| 76.5% | | Water |

Intermediate B
| | | |
|---|---|---|
| 2.5 | grams | Perfume |
| 2.0 | grams | 10% dye solution in water |
| 5.0 | grams | Ethyl Alcohol |

Intermediate C
| | | |
|---|---|---|
| 0.5 | gram | 15% basic chrome sulfate |
| 0.3 | gram | 20% aqueous solution of aluminum sulfate |
| 0.06 | gram | Sodium hexametaphosphate |
| 9.7 | grams | Water |

Each of the intermediates was prepared by adding the ingredients and stirring fully until the components were evenly dispersed. After stirring, the components of Intermediate B were added to the components of Intermediate A with good agitation. Subsequent to this agitation, Intermediate C was added to Intermediates A and B and poured into air freshener containers. The gels were formed in a sort period of time and were relatively firm, although there was some softness observed in this gel.

EXAMPLE 7

The experiment of Example 1 was repeated with the exception that the 3 grams of sodium carboxymethyl cellulose was replaced with 2 grams of potassium carboxymethyl cellulose.

The gels formed from this composition showed no signs of shrinkage or syneresis and were firm and relatively rigid and free-standing.

EXAMPLE 8

A composition having the following formulation was prepared:

| | |
|---|---|
| 3.0 parts | Medium range viscosity sodium carboxymethyl cellulose having a molecular weight of approximately 250,000 |
| 0.3 parts | Hydroxylated guar gum |
| 0.2 parts | Formaldehyde preservative |

These ingredients are fully mixed and 2 grams of perfume, 5 grams of ethyl alcohol and 0.5 gram of a 10% dye solution are added. To this mixture is added 0.6 gram of 15% basic chrome sulfate (Wayne Tan 175) and 11.9 grams of water. These gels produced were satisfactory and showed no shrinkage, brittleness or syneresis.

EXAMPLE 9

A gel formulation was prepared utilizing the procedure of Example 6 with the exception that the 2 parts of medium viscosity CMC are replaced by a mixture of 0.5 part of high viscosity CMC, molecular weight approximately 750,000, and 1.5 parts low viscosity CMC, molecular weight approximately 500,000. Again, these gels produced were satisfactory although slightly on the brittle side. There was no indication of syneresis.

COMPARATIVE EXAMPLES 1–7

The formulations shown in Table I below were prepared by first combining the components in Parts A and B. After thorough mixing, Part B was added to Part A with mixing. The composition was then poured, if possible, into air freshener gel packages of glass beakers.

TABLE I

| Comparative Example | 1 | 2 | 3 | 4 | 5 | 6 | 7 |
|---|---|---|---|---|---|---|---|
| PART A | | | | | | | |
| CMC | 3.0 | 3.0 | 3.0 | 3.0 | 3.0 | 3.0 | 3.0 |
| Preservative | 0.1 | 0.1 | — | — | — | — | 0.1 |
| Water | 82.6 | 82.6 | 82.0 | 96.9 | 96.9 | 96.9 | 81.9 |
| PART B | | | | | | | |
| Water | 7.35 | 7.35 | 9.8 | — | — | — | 13.6 |
| 1% Aqueous Dye Solution | 2.0 | 2.0 | — | — | — | — | — |
| Triton X-100[1] | 2.0 | 2.0 | 2.0 | — | — | — | — |
| Perfume | 2.0 | 2.0 | 2.5 | — | — | — | — |
| $Fe_2(SO_4)_3$[2] | 0.9 | — | — | — | — | — | — |
| $Fe(NO_3)_3$[2] | — | 0.9 | — | — | — | — | — |
| $Zn(NO_3)_2$ | — | — | 0.7 | — | — | — | — |
| $CuSO_4$ | — | — | — | 0.1 | — | — | — |
| $Zn(OAc)_2$ | — | — | — | — | 0.1 | — | — |
| $ZnSO_4$ | — | — | — | — | — | 0.1 | — |
| $Co^{+3}$[3] | — | — | — | — | — | — | 1.4 |
| Geltime | Inst | Inst | No gel | Inst | Inst | Inst | [4] |

Notes
[1] Octyl phenoxy polyethoxy ethanol
[2] 30% Aqueous solution
[3] Prepared by oxidizing 1.0 g. of $Co(OAc)_2 \cdot 4H_2O$ with 0.4 g. $H_2O_2$
[4] Gel forms in 15 minutes, but reverts to liquid in 2 days.

As can be seen from the above table, the trivalent and divalent iron, zirconium, copper, zinc and cobalt did not form satisfactory gels because of instability, i.e., cobalt or instant gelling with the CMC. Attempts were also made to retard the gel times using sequestering agents. However, the sequestering agents were either not effective or prevented gelling altogether.

EXAMPLES 10–16

The formulations as shown in Table II below were prepared using different viscosity CMC. The formulations were prepared by combining the components of Parts A and B followed by adding Part B to Part A with good mixing. The compositions were poured, if possible, into air freshener containers or glass beakers.

TABLE II

| EXAMPLES | 10 | 11 | 12 | 13 | 14 | 15 | 16 |
|---|---|---|---|---|---|---|---|
| PART A | | | | | | | |
| Water | 84.15 | 82.65 | 96.7 | 96.7 | 84.7 | 82.55 | 98.0 |
| Preservative | 0.05 | 0.05 | — | — | 0.05 | 0.05 | — |
| CMC (B50) | 1.50 | 3.00 | — | — | — | — | — |
| CMC (7LF) | — | — | 3.0 | — | — | 1.5 | — |
| CMC (7HCP) | — | — | — | 3.0 | 1.00 | 1.5 | 1.5 |
| PART B | | | | | | | |
| Chrome 33% | 0.30 | 0.30 | 0.30 | 0.30 | 0.25 | 0.40 | 0.5 |
| Triton X-100 | 2.00 | 2.00 | — | — | 2.00 | 2.00 | — |
| 1% Dye in $H_2O$ | 10.00 | 10.00 | — | — | 10.00 | 10.00 | — |
| Perfume | 2.00 | 2.00 | — | — | 2.00 | 2.00 | — |
| Gelling Time | 25 min. | 10 min. | 30 min. | 35 sec. | 1 min. | 30 min. | 10 min. |
| Syneresis (72 hr.) | Slight | Nil | Nil | Nil | Nil | Nil | Moderate |

As can be seen, the amount and viscosity of the CMC does effect the gelling time, compare Examples 11 and 12. However, each gel produced had good properties and low or no syneresis except for Example 16 which had a CMC to trivalent metal oxide ratio outside the preferred range of the present invention. Even though there was syneresis present, for some applications this system could be used.

EXAMPLES 17–21

The formulations shown in Table III below were prepared as in Examples 9–14 above.

TABLE III

| EXAMPLES | 17 | 18 | 19 | 20 | 21 |
|---|---|---|---|---|---|
| PART A | | | | | |
| Water | 83.8 | 82.3 | 83.5 | 76.5 | 79.35 |
| Preservative | 0.2 | 0.2 | 0.2 | 0.2 | — |
| CMC (7L) | — | 0.75 | — | — | — |
| CMC (7M) | — | — | — | 3.0 | — |
| CMC (7H) | 1.35 | 0.75 | 1.0 | — | 0.5 |
| Hydroxylated Guar | — | 0.5 | 0.3 | 0.3 | 0.15 |
| PART B | | | | | |
| Water | 10.29 | 7.35 | 7.78 | 13.41 | 12.92 |
| Pluronic L64 | 2.0 | — | — | — | — |
| Chrome 15% | — | — | — | 0.4 | — |
| Chrome WT175 | 0.5 | 0.5 | 0.4 | — | 0.2 |
| 20% Solution of $Al_2(SO_4)_3$ | — | — | — | 0.3 | — |
| Perfume | 1.8 | 2.5 | 1.8 | 0.75 | 1.8 |
| Dye | 0.05 | 0.15 | 0.02 | 0.08 | 0.08 |
| Na Hexametaphosphate | 0.06 | — | — | 0.06 | — |
| Ethanol | — | 5.0 | 5.0 | 5.0 | 5.0 |
| Gelling Time | 20 min. | 20 min. | 30 min. | 35 min. | 40 min. |
| Syneresis | Nil | Nil | Nil | Nil | Nil |

The compositions of Examples 16–19 had no surfactant but included a guar gum derivative. The perfume was evenly distributed throughout the gel. Example 19 was not strong enough to be self-supporting but was a relatively firm gel, suitable for use in a tub or beaker-like container.

EXAMPLES 22–25

To show the effect of differing degrees of substitution of CMC on the gels of the present invention, a series of gels were prepared having a similar molecular weight range as in Example 1 using the following formulation:

| | |
|---|---|
| Intermediate A | |
| CMC | 3.00 |
| $H_2O$ | 82.00 |
| Intermediate B | |
| Basic Chrome Sulfate (15% $Cr_2O_3$) | 0.60 |
| $H_2O$ | 14.40 |
| | 100.00 |

The results are shown in Table IV.

TABLE IV

| Example | Degree of Subs. | Results |
|---|---|---|
| 22 | 0.4 | Lower flexibility |
| 23 | 0.7 | Firm, less flexible |
| 24 | 0.9 | Firm, slightly less flexible |
| 25 | 1.2 | Firm and flexible |

As can be seen from the above, the gels formed using CMC with a degree of substitution of 0.4 are less flexible, although still usable, than the other gel and the flexibility increases with the degree of substitution.

Although the air freshener gels have been described with reference to the foregoing specific embodiments, these embodiments and examples are for illustration only and should in no way be considered as limiting the present invention which is described in the appended claims.

What is claimed is:

1. An air freshener gel composition consisting essentially of in an aqueous system from 0.5–10% by weight of carboxymethyl cellulose selected from sodium carboxymethyl cellulose and potassium carboxymethyl cellulose; from 0.01–10% by weight of perfume; from 0.05–10% of a surfactant; a source of trivalent cations selected from chromic ions, aluminum ions and mixtures sufficient to produce a weight ratio of carboxymethyl cellulose to effective weight of trivalent cation of 1:0.01 to 1:0.1 and water to 100%.

2. The composition of claim 1 wherein said source of cations is selected from basic chrome sulfate, chromium acetate, aluminum sulfate, aluminum acetate and mixtures.

3. The composition of claim 2 wherein said source of trivalent cations is basic chrome sulfate.

4. The composition of claim 1 wherein said trivalent cation is the chromic ion.

5. The composition of claim 1 wherein said composition additionally included 1–7% of a lower monhydric alcohol having 1–4 carbon atoms.

6. The composition of claim 1 wherein said ratio is 1:0.03 to 1:0.06.

7. The composition of claim 1 wherein said surfactant is selected from nonionic surfactants and nonionic hydrocolloid surfactants.

8. The composition of claim 7 wherein said surfactant is a nonionic surfactant.

9. The composition of claim 1 which includes from 0–0.5% of a sequestering agent.

10. A method for dispensing a perfume over an extended period of time at a controlled rate comprising exposing a gel comprising in an aqueous system from 0.5–10% by weight of carboxymethyl cellulose; from 0.01–10; % by weight of perfume; from 0.05–10% of a surfactant; a source of trivalent cations selected from chromic ions, aluminum ions and mixtures sufficient to produce a weight ratio of carboxymethyl cellulose to effective weight of trivalent cation of 1:0.01 to 1:0.1 and water to 100% to the atmosphere and allowing the water in said gel to evaporate.

* * * * *